(12) United States Patent
Wiley, Jr. et al.

(10) Patent No.: US 8,981,079 B2
(45) Date of Patent: Mar. 17, 2015

(54) PURIFICATION OF TERTIARY FORMAMIDE CONTAMINATED WITH TERTIARY ACETAMIDE

(75) Inventors: James Edwin Wiley, Jr., Moraga, CA (US); Mohamad R. Jaber, Rancho Cucamonga, CA (US)

(73) Assignee: Tate & Lyle Technology Limited, London (GB)

( * ) Notice: Subject to any disclaimer, the term of this patent is extended or adjusted under 35 U.S.C. 154(b) by 467 days.

(21) Appl. No.: 13/378,531

(22) PCT Filed: Jun. 18, 2010

(86) PCT No.: PCT/US2010/039142
§ 371 (c)(1),
(2), (4) Date: Mar. 13, 2012

(87) PCT Pub. No.: WO2010/151489
PCT Pub. Date: Dec. 29, 2010

(65) Prior Publication Data
US 2012/0157675 A1    Jun. 21, 2012

Related U.S. Application Data

(60) Provisional application No. 61/219,133, filed on Jun. 22, 2009.

(51) Int. Cl.
*C07H 5/02* (2006.01)
*C07C 233/03* (2006.01)
*C07C 231/24* (2006.01)
*C07H 1/06* (2006.01)

(52) U.S. Cl.
CPC ............... *C07C 231/24* (2013.01); *C07H 1/06* (2013.01); *C07H 5/02* (2013.01)
USPC .......... 536/122; 536/123.1; 536/18.5; 514/53

(58) Field of Classification Search
CPC ........ A61K 8/60; A61K 31/70; C07C 231/24; C07C 233/03; C07H 1/06; C07H 3/04; C07H 5/02
USPC .............. 536/4.1, 18.5, 115, 122, 123.1, 124; 514/53
See application file for complete search history.

(56) References Cited

U.S. PATENT DOCUMENTS

| 4,380,476 A | 4/1983 | Mufti et al. |
| 4,783,526 A | 11/1988 | O'Brien et al. |
| 4,889,928 A | 12/1989 | Simpson |
| 4,950,746 A | 8/1990 | Navia |
| 4,980,463 A * | 12/1990 | Walkup et al. ............... 536/124 |
| 5,023,329 A | 6/1991 | Neiditch et al. |
| 5,034,551 A | 7/1991 | Vernon et al. |
| 5,089,608 A | 2/1992 | Walkup et al. |
| 5,440,026 A | 8/1995 | Khan et al. |
| 5,470,969 A | 11/1995 | Sankey et al. |
| 5,498,709 A * | 3/1996 | Navia et al. ................... 536/124 |
| 5,530,106 A | 6/1996 | Navia et al. |
| 6,939,962 B2 | 9/2005 | Clark et al. |
| 2005/0170069 A1 | 8/2005 | Vernon et al. |
| 2006/0205936 A1 | 9/2006 | Jia et al. |
| 2006/0276639 A1 | 12/2006 | Fry |
| 2007/0100139 A1 | 5/2007 | Fry |
| 2007/0227897 A1 | 10/2007 | Li et al. |
| 2008/0227971 A1 | 9/2008 | Leinhos et al. |
| 2009/0264633 A1 | 10/2009 | Kerr et al. |

FOREIGN PATENT DOCUMENTS

| CN | 101386632 A | 9/2007 |
| CN | 101328195 A | 12/2008 |
| CN | 101460447 A | 6/2009 |
| EP | 0 708 110 A2 | 4/1996 |
| WO | WO 2005/090374 | 9/2005 |
| WO | WO 2005/090376 | 9/2005 |
| WO | WO 2007/023505 A2 | 3/2007 |
| WO | WO 2007/026377 A2 | 3/2007 |
| WO | WO 2007/052304 A2 | 5/2007 |
| WO | WO 2008/015694 A2 | 2/2008 |

OTHER PUBLICATIONS

Ault, A. Techniques and Experiments for Organic Chemistry, 5th Ed., 1994, pp. 72-74.*
International Search Report dated Aug. 10, 2010.
British Patent Office Search Report dated May 24, 2010 (1).
British Patent Office Search Report dated May 24, 2010 (2).
"Dimethyl Formamide )DMF)" [online]; available from http://www.refltd.com/index.php/products/ind-products/79-dmf; Accessed May 20, 2010. See especially "DMAC impurity in DMF" (see table) and "Uses" No. 7.

(Continued)

*Primary Examiner* — Ganapathy Krishnan
(74) *Attorney, Agent, or Firm* — RatnerPrestia

(57) ABSTRACT

A chlorinating agent such as a chloroiminium species is used to remove or neutralize tertiary acetamide present as a contaminant in a tertiary formamide solvent. Tertiary formamide solvent purified or treated in this manner can be used as a reaction vehicle for the chlorination of sucrose-6-acylates, thereby improving the yields of the desired sucralose-6-acylate (an intermediate in the production of sucralose).

31 Claims, No Drawings

(56) References Cited

OTHER PUBLICATIONS

"Dimethylformamide" [online]; available from http://web.archieve.org/web/20040302064806/http:www.filochemical.com/pape31.html; accessed May 21, 2010; published Mar. 2, 2004. See especially "Quality specifications" relating to DMAC.

"Dimethylformamide" [online]; available from http://www.ec21.com/product-details/Dimethylformamide--4316968.html; accessed May 20, 2010. See especially "Dimethyl Acetamide (DMAC) mg/kg <200".

"DMF/dimethylformamide/dmf" [online]; available from http://www.alibaba.com/product/tr110902426-110433932-0/DMF_Dimethylformamide-dmf.html; accessed May 20, 2010. See especially DMAC ppm.

Second Office Action issued by the Chinese Patent Office for Application No. 201080027613.4 Dated Jul. 23, 2014 (w/English language translation).

\* cited by examiner

PURIFICATION OF TERTIARY FORMAMIDE CONTAMINATED WITH TERTIARY ACETAMIDE

CROSS REFERENCE TO RELATED APPLICATIONS

This application is the national phase filing of International patent application No. PCT/US2010/039142, filed 18 Jun. 2010 and published in English on 29 Dec. 2010 as WO 2010/151489, which claims priority from U.S. Appln. No. 61/219,133, filed 22 Jun. 2009, each of which is incorporated herein by reference in its entirety for all purposes.

BACKGROUND OF THE INVENTION

This invention relates to the purification of tertiary formamides such as dimethylformamide that are contaminated with tertiary acetamides such as dimethylacetamide. The invention further relates to improved methods of chlorinating sucrose-6-acylates, which are useful intermediates in the production of sucralose.

Sucralose (4,1',6'-trichloro-4,1',6'-trideoxygalactosucrose), a high-intensity sweetener made from sucrose, can be used in many food and beverage applications.

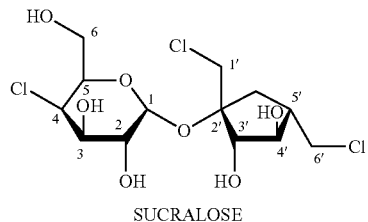

SUCRALOSE

A number of different synthesis routes for the preparation of sucralose have been developed in which the reactive hydroxyl in the 6 position is first blocked with an acyl group to form a sucrose-6-acylate. The acyl group can be any acyl group that serves to protect the 6-hydroxy group during chlorination. It is preferably an aliphatic or carbocyclic aromatic acyl group, more preferably a benzoyl or acetyl group, and most preferably an acetyl group. The sucrose-6-acylate is chlorinated to replace the hydroxyl groups at the 4,1' and 6' positions with chlorine atoms to produce 4,1',6'-trichloro-4,1',6'-trideoxygalactosucrose 6-acylate (referred to herein as sucralose-6-acylate), followed by hydrolysis to remove the acyl substituent and thereby produce sucralose. Several synthesis routes for formation of the sucrose-6-acylates involve tin-mediated acylation reactions, with illustrative examples being disclosed in U.S. Pat. Nos. 4,950,746; 5,023,329; 5,089,608; 5,034,551; and 5,470,969, all of which are incorporated herein by reference in their entirety for all purposes.

Various chlorinating agents may be used to chlorinate the sucrose-6-acylate, and most commonly a Vilsmeier-type salt such as Arnold's Reagent (N,N-dimethylchloroformiminium chloride) will be used. One suitable chlorination process is disclosed by Walkup et al. (U.S. Pat. No. 4,980,463), incorporated herein by reference in its entirety for all purposes. This process uses a tertiary formamide, typically N,N-dimethyl formamide ("DMF"), as the chlorination reaction solvent. After the chlorination is complete, adducts of Arnold's Reagent on the base sucrose moiety and excess chlorinating reagent are neutralized ("quenched") with aqueous base to provide the sucralose-6-acylate in an aqueous solution, accompanied by the tertiary amide solvent and salts resulting from reactions of the chlorination reagent. The sucralose-6-acylate is then deacylated to produce sucralose. One suitable deacylation process is taught by Navia et al., U.S. Pat. No. 5,498,709, the entire disclosure of which is incorporated herein by reference in its entirety for all purposes.

In commercial processes, it will be economically desirable to recover the tertiary formamide solvent from sucrose-6-acylate reaction product mixtures (either directly after chlorination or after one or more subsequent processing/reaction steps) and then recycle such recovered tertiary formamide for use as a reaction vehicle (e.g., as a reaction vehicle for the sucrose-6-acylate chlorination and/or the esterification of sucrose to obtain the sucrose-6-acylate). As used herein, the term "reaction vehicle" means a diluent or solvent in which a reaction is carried out; the diluent or solvent does not necessarily fully dissolve all the components being reacted or all the products produced in the reaction. However, depending upon the particular reagents and processing conditions selected, the recovered tertiary formamide is typically contaminated with varying amounts of tertiary acetamides such as dimethylacetamide ("DMAc"), which can be formed as a process by-product. The level of DMAc tends to build up over time as the tertiary formamide is recycled and reused.

We have now discovered that the presence of DMAc as a contaminant in the DMF used as a reaction vehicle when chlorinating a sucrose-6-acylate has a significant, adverse effect on the yield of the desired chlorination product. For every 1 weight % of DMAc present in the DMF, a product yield loss of approximately 8 to 10% is observed (i.e., the yield decreases from ca. 60% to ca. 50-52%) when carrying out a chlorination process in accordance with the process described in the aforementioned Walkup et al. patent. This suggests that DMAc actively participates in some way during such chlorination so as to interfere with the desired conversion of hydroxyl groups in the sucrose-6-acylate to chloride groups. The adverse effect of DMAc on the product yield obtained when chlorinating a sucrose-6-acylate using DMF as a reaction vehicle was surprising, in view of the fact that tertiary amides in general have previously been proposed as suitable solvents for use in such a chlorination process.

We have now found that reducing the level of DMAc in a DMF-containing stream recovered from a sucrose-6-acylate chlorination process prior to reusing that stream as a reaction vehicle provides enhancements in the yield of the desired sucralose-6-acylate. That is, managing the DMAc content in such a recycle stream helps to ensure that the sucralose-6-acylate yield remains about the same as it would be using pure DMF as a reaction vehicle. Unfortunately, because DMF and DMAc have similar properties and close boiling points (153° C. and 166° C. respectively, at atmospheric pressure), purifying the recovered DMF stream by fractional distillation is difficult, energy intensive, and requires expensive distillation equipment, thereby increasing the cost of manufacturing sucralose.

Accordingly, it would therefore be quite desirable to develop alternative, less expensive methods of purifying DMF to remove DMAc or to develop ways of using DMAc-contaminated DMF in a sucrose-6-acylate chlorination process while preserving the yields that are possible when pure DMF is used as solvent.

SUMMARY OF THE INVENTION

In one aspect, the present invention provides a process comprising:

a) recovering (by distillation, for example) a crude recycle solvent stream comprising a tertiary formamide and a tertiary acetamide from a mixture comprising at least one substance less volatile than the tertiary formamide and the tertiary acetamide (e.g., a sucrose moiety-containing compound such as sucralose, chlorinated sucrose compounds other than sucralose, sucralose-6-acylate, chlorinated sucrose-6-acylate compounds other than sucralose-6-acylate, or other compounds derivable, directly or indirectly, from sucrose), said tertiary formamide and said tertiary acetamide (wherein the crude recycle solvent stream is free or essentially free of any sucrose moiety-containing compound);

b) reducing the concentration of tertiary acetamide in the crude recycle solvent stream to provide a purified recycle solvent stream; and c) recycling said purified recycle solvent stream for use as a reaction vehicle.

In another aspect, the present invention provides a method wherein a contaminated tertiary formamide containing a tertiary acetamide as a contaminant is contacted with a chlorinating agent such as a chloroiminium species under conditions effective to selectively react the tertiary acetamide with the chlorinating agent to form a reaction product mixture. Purified tertiary formamide can be readily recovered from the reaction product mixture by distillation.

In still another aspect, a method for producing a sucralose-6-acylate is provided. This method comprises a) forming a mixture of a sucrose-6-acylate in a reaction vehicle comprised of a tertiary formamide and a tertiary acetamide; b) analyzing said reaction vehicle or said mixture to determine the amount of tertiary acetamide contained therein; and c) contacting said mixture with a quantity of a chlorinating agent under conditions effective to react said tertiary acetamide and said sucrose-6-acylate with said chlorinating agent, wherein said quantity of said chlorinating agent is selected in accordance with the amount of tertiary acetamide contained in said reaction vehicle or said mixture. That is, the quantity of chlorinating agent is increased when the reaction vehicle or mixture is determined to have a relatively high concentration of tertiary acetamide, thereby at least partially compensating for the loss in the yield of sucralose-6-acylate that would otherwise occur due to the competing reaction of the chlorinating agent with the tertiary acetamide.

DETAILED DESCRIPTION OF THE INVENTION

Tertiary formamides capable of being purified or utilized in accordance with the present invention include any of the N-formyl amides known in the art where the nitrogen atom is substituted with two alkyl and/or aryl groups. Dimethylformamide is a particularly suitable tertiary formamide. Other tertiary formamides include N-formylpiperidine, N-formylmorpholine, and N,N-diethylformamide.

The tertiary acetamide present initially as a contaminant in the tertiary formamide will typically be an N-acetyl amide that is an analog of the tertiary formamide. In the case where dimethylformamide is the tertiary formamide, for example, the tertiary acetamide contaminant may be dimethylacetamide. Typically, the tertiary acetamide is a relatively minor component of the contaminated tertiary formamide, which in one embodiment of this invention is recovered from a sucrose-6-acylate chlorination reaction product mixture and is intended to be recycled and reused in such a chlorination process. For example, the contaminated tertiary formamide may comprise from about 0.5 to about 7 weight percent tertiary acetamide with the balance being predominately tertiary formamide (although other components could also be present in small amounts, e.g., less than about 5 weight percent or less than about 2 weight percent in total). In various embodiments of the invention, the contaminated tertiary formamide or the crude recycle solvent stream is comprised of at least 0.5 weight percent tertiary acetamide, or at least 0.8 weight percent tertiary acetamide, or at least 1.0 weight percent tertiary acetamide.

The chlorinating agent used in the present invention may be any species capable of reacting with a tertiary acetamide in the presence of a tertiary formamide to convert the tertiary acetamide to a product capable of being separated from the tertiary formamide, using a separation method such as flash distillation for example. In one embodiment, the chlorinating agent is a chloroiminium species. Preferably, the chloroiminium species is a reagent of the Vilsmeier type, e.g., an N,N-dialkyl(chloroformiminium) chloride or N,N-alkylaryl(chloroformiminium) chloride represented by the following formula:

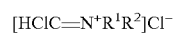

$$[HClC=N^+R^1R^2]Cl^-$$

wherein $R^1$ and $R^2$ are the same or different, and each independently represents an alkyl group typically having 1 to 4 carbon atoms; alternatively, $R^1$ represents an alkyl group and $R^2$ represents a phenyl group.

A Vilsmeier reagent may be prepared by one of various methods, for example, by a reaction of an N-formyl amide, such as DMF, and a chlorinating agent, such as phosgene ($COCl_2$), phosgene dimer (Cl—CO—O—$CCl_3$), phosgene trimer ($Cl_3$C—O—CO—O—$CCl_3$), oxalyl chloride (Cl—CO—CO—Cl), phosphorus pentachloride ($PCl_5$), phosphorus oxychloride ($POCl_3$), or thionyl chloride ($SOCl_2$). The chloroiminium species may be generated in situ, for example by adding a chlorinating agent to the tertiary acetamide-contaminated tertiary formamide (whereby the chloroiminium species is formed by reaction of the chlorinating agent with a portion of the tertiary formamide). Alternatively, the chloroiminium species may be separately prepared and then combined with the tertiary acetamide-contaminated tertiary formamide.

Other suitable chlorinating agents include acyl chlorides, phosphorus chlorides, sulfur chlorides, and the like, such as phosgene, phosgene dimer, phosgene trimer, phosphorus pentachloride, phosphorus oxychloride, thionyl chloride, and oxalyl chloride.

In one aspect of the invention, the chlorinating agent (e.g., a chloroiminium species) may be used to carry out a purification of a tertiary acetamide-contaminated tertiary formamide prior to using the purified tertiary formamide as a solvent (as a reaction vehicle, for example). In this embodiment, the chlorinating agent is contacted with the contaminated tertiary formamide under conditions effective to react at least a portion (preferably, all or essentially all) of the tertiary acetamide to form a reaction product mixture from which purified tertiary formamide is recovered. In various embodiments of the invention, the conditions of such contacting step are selected so as to react at least 50%, 60%, 70%, 80% or 90% of the tertiary acetamide initially present in the contaminated tertiary formamide. It is believed that the chlorinating agent converts the tertiary acetamide contaminant to a less volatile species that is capable of being more readily separated from the tertiary formamide than the initially present tertiary acetamide contaminant would be. For example, following treatment of the contaminated tertiary formamide with a chloroiminium species, tertiary formamide containing a reduced amount of tertiary acetamide (or which is even free or essentially free of tertiary acetamide) may be recovered using flash or simple distillation, thereby avoiding the need to employ expensive fractional distillation equipment and processing to separate the desired tertiary formamide from the tertiary acetamide. Simple or flash distillation methods are well known in the art and can be easily adapted for use in the present invention.

Alternatively, the reaction product mixture can simply be carried forward without further treatment or separation and used as a reaction vehicle. For example, the reaction product mixture can be utilized as the reaction vehicle for chlorinating a sucrose-6-acylate to yield a sucralose-6-acylate. Methods of chlorinating sucrose-6-acylate are well known in the art and are described, for example, in U.S. Pat. No. 4,980,463; U.S. Pat. No. 4,380,476; US 2006-0205936; and US 2007-0100139, each of which is incorporated herein by reference in its entirety for all purposes. The preparation of the sucrose-6-acylate starting materials for such chlorination reactions is well-known in the art and is disclosed, for example, in U.S. Pat. No. 4,783,526; U.S. Pat. No. 4,950,746; U.S. Pat. No. 4,889,928; U.S. Pat. No. 5,023,329; U.S. Pat. No. 5,089,608; U.S. Pat. No. 5,034,551; U.S. Pat. No. 5,470,969; U.S. Pat. No. 5,440,026; U.S. Pat. No. 6,939,962; and US 2007-0227897, the disclosures of which are all incorporated herein by reference in their entirety for all purposes.

In general, it will usually be desirable to use an excess of the chlorinating agent (e.g., a chloroiminium species) relative to the amount of tertiary acetamide contaminant present in the tertiary formamide, in order to achieve complete or near complete reaction of the tertiary acetamide. Typically, for example, it will be desirable to reduce the concentration of tertiary acetamide to a level of not more than about 0.4, 0.3 or 0.2 weight percent. In certain embodiments of the invention, for example, the equivalents ratio of chlorinating agent:tertiary acetamide is at least about 1.5/n:1, or at least about 2/n:1 or at least about 2.5/n:1, wherein n is the number of chlorine atoms per molecule of chlorinating agent that are capable of reacting with the tertiary acetamide. For example, where the chlorinating agent is a chloroiminium species or phosgene, n=1. The equivalents ratio of chlorinating agent:tertiary acetamide may be within the range of about 2/n:1 to about 3.5/n:1 (e.g., the equivalents ratio of chloroiminium species or phosgene to dimethylacetamide may be about 2:1 to about 3.5:1).

The conditions under which the chlorinating agent is reacted with the tertiary acetamide-contaminated tertiary formamide are not believed to be particularly critical and will be dependent to some extent on the reactivity of the chlorinating agent selected with the tertiary acetamide. In one embodiment, the temperature is selected to be within the range where the desired reaction of the tertiary acetamide proceeds at an acceptable rate (e.g., where the reaction is substantially complete within about 3 hours) while avoiding any undesired side reactions (e.g., reaction of the tertiary formamide, other than what might occur as a result of, for example, the in situ preparation of a chloroiminium species from such tertiary formamide, where such a chloroiminium species is utilized as the chlorinating agent). For example, the chlorinating agent and the tertiary acetamide-contaminated tertiary formamide may be contacted within the temperature range of about −50° C. to about 200° C. for a period of time within the range of about 1 minute to about 1 day. In a more specific example, where the tertiary acetamide is dimethylacetamide, the tertiary formamide is dimethylformamide, and the chlorinating agent is a chloroiminium species such as Arnold's Reagent, temperatures of from about −20° C. to about 30° C. and reaction times of from about 5 minutes to about 2 hours are typically suitable. The chlorinating agent may be added in portions or incrementally to the contaminated tertiary formamide. Agitation or stirring of the contaminated tertiary formamide while it is being contacted with the chlorinating agent will generally be desirable.

In another aspect of the invention, a method for producing a sucralose-6-acylate is provided wherein a mixture of a sucrose-6-acylate in a reaction vehicle comprised of tertiary formamide and tertiary acetamide is contacted with a chlorinating agent (e.g., a chloroiminium species) under conditions effective to react the tertiary acetamide and the sucrose-6-acylate with the chlorinating agent (e.g., at a temperature within the range of about −50° C. to about 200° C. for a period of time within the range of about 1 minute to about 1 day, depending upon the reactivity of the particular chlorinating agent selected as well as other factors). In this embodiment of the invention, the chlorinating agent is used to both remove the tertiary acetamide as a contaminant (by converting the tertiary acetamide to a different species which is non-reactive with the chlorinating agent) and to introduce chlorine atoms onto the sucrose-6-acylate. Such a process may be carried out in a step-wise manner. For example, the mixture may be contacted with the chlorinating agent under a first set of conditions effective to react the chlorinating agent with the tertiary acetamide and then under a second set of conditions effective to achieve chlorination of the sucrose-6-acylate. The first set of conditions typically will include a reaction temperature that is lower than the reaction temperature utilized in the second set of conditions. To illustrate this embodiment, the mixture may be first contacted with a chloroiminium species as a chlorinating agent at a temperature within the range of from about −20 to about 30° C. Within such temperature range, the chloroiminium species reacts with the tertiary acetamide, although the chloroiminium species may also react with the hydroxyl groups of the sucrose-6-acylate to form an adduct. Generally, however, chlorination of the sucrose-6-acylate (i.e., substitution of the hydroxyl groups with chlorine atoms) is limited under the first set of conditions. After allowing all or substantially all of the tertiary acetamide to react (typically, this may take from about 5 minutes to about 12 hours), the temperature of the reaction mixture may be increased to a temperature sufficient to effect the desired chlorination of the sucrose-6-acylate (with the reaction mixture typically being maintained at this higher temperature for a period of time ranging from about 5 minutes to about 18 hours). A number of reaction conditions can be used to achieve such chlorination. For example, U.S. Pat. No. 4,980,463 (incorporated herein by reference in its entirety for all purposes) describes a two stage process in which chlorination of sucrose-6-acylate is carried out at two different temperatures: a temperature not higher than about 85° C. and a temperature of at least about 100° C. but not higher than about 130° C. As another example, U.S. Published Application 2007/0100139 (incorporated herein by reference in its entirety for all purposes) discloses a process in which the reaction mixture is heated between 75° C. and 100° C. to effect chlorination. In general, reaction temperatures between about 85° C. and 130° C. are preferred in order to secure a high yield of the desired sucralose-6-acylate, although in some situations an initial reaction temperature that is below this range may provide certain advantages.

The chloroiminium species may be generated in situ, for example by adding a chlorinating agent such as phosgene to a mixture of a sucrose-6-acylate and a tertiary acetamide-contaminated tertiary formamide (whereby the chloroiminium species is formed by reaction of the chlorinating agent with a portion of the tertiary formamide). Alternatively, the chloroiminium species may be separately prepared and then combined with the mixture of sucrose-6-acylate and tertiary acetamide-contaminated tertiary formamide. In one embodiment, a tertiary acetamide-contaminated tertiary formamide is first treated with a chlorinating agent and thereafter combined with the sucrose-6-acylate. For example, phosgene may be combined with the tertiary acetamide-contaminated tertiary formamide and allowed to react and form a chloroformiminium chloride salt with part of the tertiary formamide. The chloroformiminium chloride salt reacts with the tertiary acetamide, with the resulting mixture thereafter being contacted and reacted with sucrose-6-acetate or sucrose-6-benzoate (the sucrose-6-acylate may be added to the mixture, or the mixture may be added to the sucrose-6-acylate). In another embodiment, a mixture of sucrose-6-acylate and tertiary acetamide-contaminated tertiary formamide is treated with the chlorinating agent (e.g., a chloroiminium species or phosgene).

One embodiment of the invention provides a method for producing a sucralose-6-acylate, wherein the method comprises at least the steps of:
  a). forming a mixture of a sucrose-6-acylate in a reaction vehicle comprised of a tertiary formamide and a tertiary acetamide;
  b). analyzing the reaction vehicle or the mixture to determine the amount of tertiary acetamide contained therein; and
  c). contacting the mixture with a quantity of a chlorinating agent under conditions effective to react the tertiary acetamide and the sucrose-6-acylate with the chlorinating agent, wherein the quantity of said chlorinating agent is selected in accordance with the amount of tertiary acetamide contained in the reaction vehicle or the mixture.

The amount of tertiary acetamide in the reaction vehicle or mixture may be readily measured using any suitable analytical method, such as, for example, gas chromatography. The tertiary acetamide concentration thereby determined is utilized to adjust the quantity of chlorinating agent contacted with the mixture, thereby improving the yield of sucralose-6-acylate obtained as a result of the chlorination reaction while also avoiding unnecessary production costs. For example, if the tertiary acetamide content measured is relatively high, then a larger quantity of chlorinating agent is utilized in step c) to help compensate for the competing reaction of the tertiary acetamide with the chlorinating agent that will take place and that would reduce the amount of chlorinating agent that is available to chlorinate the sucrose-6-acylate. However, if the tertiary acetamide content in the reaction vehicle or mixture is relatively low, then the quantity of chlorinating agent employed can correspondingly be reduced, thereby avoiding the wasteful use of excess chlorinating agent that will not significantly improve the yield of the desired sucralose-6-acylate. Thus, the equivalents of chlorinating agent used can be adjusted in response to the measured levels of tertiary acetamide in a recycled tertiary formamide-containing stream being employed as a reaction vehicle in a sucrose-6-acylate chlorination process.

In one aspect of the invention, a molar amount of the chlorinating agent is used that is greater than or equal to:
$7 \cdot 1/n \cdot$(molar amount sucrose-6-acylate)$+2 \cdot 1/n \cdot$(molar amount tertiary acetamide)
wherein n is the number of chlorine atoms per molecule of chlorinating agent that are capable of participating in a chlorination reaction with the sucrose-6-acylate and the tertiary acetamide. For example, where the chlorinating agent is a chloroiminium species or phosgene, n=1.

In another aspect, a molar amount of the chlorinating agent is used that is within the range:
$[7 \cdot 1/n \cdot$(molar amount sucrose-6-acylate)$+2 \cdot 1/n \cdot$(molar amount tertiary acetamide)] to
$[8 \cdot 1/n \cdot$(molar amount sucrose-6-acylate)$+3.5 \cdot 1/n \cdot$(molar amount tertiary acetamide)]
wherein n is the number of chlorine atoms per molecule of chlorinating agent that are capable of participating in a chlorination reaction with the sucrose-6-acylate and the tertiary acetamide.

Following chlorination, the reaction mixture thereby obtained may be subsequently treated and processed in accordance with any of the methods known in the art for producing and purifying sucralose and recovering the solvent and perhaps other materials used in such methods. For example, the chlorination reaction mixture may be neutralized ("quenched") with aqueous base to provide the sucralose-6-acylate in an aqueous solution. The sucralose-6-acylate can then be deacylated to produce sucralose. The tertiary formamide solvent may be recovered by distillation (e.g., steam stripping) of the aqueous solution or at other steps in the sucralose synthesis and purification process and then recycled for use in further sucrose-6-acylate chlorination reactions. If the recovered tertiary formamide solvent is contaminated with an unacceptably high level of tertiary acetamide, it may be subjected to purification to reduce the tertiary acetamide concentration by separating or reacting the tertiary acetamide in accordance with the present invention prior to reusing the solvent as a reaction vehicle.

Methods for treating and processing reaction mixtures containing tertiary formamide solvent and sucralose-6-acylate obtained by chlorination of sucrose-6-acylate are described in the following patents and applications, each of which is incorporated herein by reference in its entirety for all purposes: US 2007-0100139; U.S. Pat. No. 4,980,463; U.S. Pat. No. 5,498,709; U.S. Pat. No. 5,530,106; US 2006-0276639; US 2005-0170069; US 2008-0227971; and US 2009-0264633.

The aforedescribed methods and steps wherein a contaminated tertiary formamide containing tertiary acetamide as a contaminant is treated to react the tertiary acetamide so as to provide a tertiary formamide having a reduced content of tertiary acetamide may be utilized in an integrated process for the production of sucralose (including the production of intermediates useful for manufacturing sucralose). This process may comprise the steps of:
  a) recovering a crude recycle solvent stream comprising a tertiary formamide and a tertiary acetamide by distillation from a mixture comprising at least one substance less volatile than the tertiary formamide and the tertiary acetamide (e.g., a sucrose moiety-containing compound), said tertiary formamide and said tertiary acetamide (wherein the crude recycle solvent stream is free or essentially free of any sucrose moiety-containing compound);
  b) reducing the concentration of tertiary acetamide in the crude recycle solvent stream to provide a purified recycle solvent stream; and
  c) recycling said purified recycle solvent stream for use as a reaction vehicle.

Step a) may be practiced by adaptation of any of the methods known in the art for recovering the solvent that has been used as a reaction vehicle for the chlorination of a sucrose-6-acylate. Distillation techniques are especially suitable, wherein a distillate stream comprising tertiary formamide and tertiary acetamide is taken overhead, with the components of the initial mixture that are less volatile than the tertiary formamide and tertiary acetamide recovered as part of the distillation bottoms. For example, the distillate stream preferably is free or essentially free of any sucrose moiety-containing compounds such as sucralose-6-acylate.

To illustrate this embodiment of the invention, a sucrose-6-acylate may be reacted with a chlorinating agent in a reaction vehicle comprising a tertiary formamide under conditions effective to produce a product stream comprising sucralose-6-acylate, the tertiary formamide, a tertiary acetamide contaminant, and, typically, other reaction products and by-products such as chlorinated sucrose-6-acylates other than sucralose-6-acylate. As mentioned previously, under certain conditions tertiary acetamide is generated during chlorination. However, it is also possible that at least some of the tertiary acetamide in the product stream was present in the initial reaction vehicle before chlorination (although, as described elsewhere in this application, if the reaction vehicle is contaminated with tertiary acetamide, it is advantageous to reduce the level of such contaminant prior to carrying out chlorination of the sucrose-6-acylate or to use a larger excess of a chlorinating agent in the chlorination to compensate for the adverse effect of the tertiary acetamide on the yield of sucralose-6-acylate).

The aforedescribed product stream can be quenched with aqueous base. In one embodiment, a portion of the tertiary formamide (together with a portion of the tertiary acetamide present as a contaminant) is removed (i.e., separated from the sucralose-6-acylate) prior to the quenching step, as described for example in U.S. Provisional Application No. 61/164,703, filed Mar. 30, 2009 (the disclosure of which is incorporated herein by reference in its entirety for all purposes). Removal of the tertiary formamide and tertiary acetamide may be accomplished by distillation, including distillation under reduced pressure. The recovered distillate (which is preferably free or essentially free of sucralose-6-acylate) can then be utilized as the crude recycle solvent stream in accordance with the present invention, wherein the tertiary acetamide concentration is reduced to provide a purified recycle solvent stream that can be recycled for use as a reaction vehicle. It may be desirable to subject the crude recycle solvent stream to other or additional purification steps prior to such reuse; for example, if the crude recycle solvent stream contains hydrogen chloride, it may be treated with a base to remove or neutralize the hydrogen chloride.

In another embodiment, the product stream comprising sucralose-6-acylate, tertiary formamide, tertiary acetamide, and possibly other reaction products and by-products is quenched with an aqueous base or the like prior to removing the tertiary acetamide-contaminated tertiary formamide to provide a product stream additionally comprising water. The sucralose-6-acylate may be deacylated (to form sucralose) before or after removal of the tertiary formamide. The removal of the tertiary formamide (typically together with tertiary acetamide as a contaminant) from this water-containing product stream may be carried out by steam stripping. Such methods are described for example in U.S. Pat. Nos. 5,498,709 and 5,530,106 (the disclosures of which are each incorporated herein by reference in their entirety for all purposes). Other removal methods could also be used, such as fractional distillation or extraction using a non-polar organic solvent. Still another possible procedure would be to remove all liquids after quench of the chlorination reaction (using an agitated thin film dryer or spray dryer, for example) to provide a solid residue from which sucralose is then recovered, as described in WO 2005/090376 and WO 2005/090374 (each of which is incorporated herein by reference in its entirety for all purposes). The recovered liquids can be utilized as the source of the crude recycle solvent stream. If needed or desired, the distillate or other liquids recovered by practice of the aforementioned procedures (e.g., the steam distillate or the organic solvent-containing extract) may be subjected to further processing so as to provide the crude recycle solvent stream that will be treated to reduce the tertiary acetamide concentration prior to recycle and reuse as a reaction vehicle in accordance with the present invention. For example, the water present in the steam distillate may be removed prior to separating the tertiary acetamide from the tertiary formamide or treating the mixture to convert the tertiary acetamide to a species that will not interfere with a sucrose-6-acylate chlorination reaction when the recycled tertiary formamide is reused as a reaction vehicle.

Reducing the concentration of tertiary acetamide in the crude recycle solvent stream to provide a purified recycle solvent stream may be carried out by any suitable method, but preferably such reduction is accomplished by a process comprising contacting the crude recycle solvent stream with a chlorinating agent such as a chloroiminium species under conditions effective to react the tertiary acetamide contaminant with the chlorinating agent in accordance with the present invention as previously described (e.g., about −50° C. to about 200° C. for about 5 minutes to about 1 day). The reaction product mixture thereby obtained may be directly used (without further processing) as a reaction vehicle. Alternatively, the tertiary formamide may be separated from the reaction product mixture by a suitable method such as distillation, wherein the less volatile product(s) formed by reaction of the chlorinating agent with the tertiary acetamide are retained as distillation bottoms and the purified recycle solvent stream recovered as the distillate and then recycled for use as a reaction vehicle.

In various embodiments of the invention, the amount of residual tertiary acetamide present in the purified recycle solvent stream is advantageously no greater than about 0.4, 0.3 or 0.2 weight percent. Such levels are typically significantly lower than the concentration of tertiary acetamide present initially in the contaminated tertiary formamide from which the purified recycle solvent stream has been obtained. For example, the tertiary acetamide concentration in the crude recycle solvent stream or contaminated tertiary formamide may be reduced by at least about 50%, 60%, 70%, 80% or 90%.

The purified recycle solvent stream may be used as a reaction vehicle in any reaction or process where it is desired to use a tertiary formamide solvent, but in one particularly advantageous embodiment the purified recycle solvent stream is utilized as a reaction vehicle in one or more steps of a sucralose production process. For example, the purified recycle solvent stream may be used as a reaction vehicle when sucrose is acylated to form a sucrose-6-acylate and/or when sucrose-6-acylate is chlorinated to form sucralose. Fresh portions of pure tertiary formamide may be combined with the purified recycle solvent stream to provide the reaction vehicle, if so desired (to make up for any losses of tertiary formamide in the sucralose production process or subsequent solvent recovery, purification, and recycle steps, for example).

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

Example 1

A 250 mL round bottom flask equipped with a stir bar was charged with 97.0 grams of reagent grade dimethylformamide (DMF) and 3.0 grams of dimethylacetamide (DMAc) (34.4 mmols.). The mixture was cooled to 0° C., and 8.4 grams of Arnold's Reagent (68.9 mmols.) was added portionwise. After addition was complete, the mixture was stirred for 45 minutes at 0° C., and the solvent was collected under vacuum using a rotary evaporator. The recovery of DMF was 87 grams, and analysis indicated that the recovered DMF was DMAc-free.

Example 2

A 250 mL round bottom flask equipped with a stir bar was charged with 13.0 grams of Arnold's Reagent (AR) (0.101 mol). Crude DMF (100.0 grams) containing 4.4% by weight DMAc (50.4 mmol) was added at room temperature. After addition was complete, mixture was stirred for 2 hours, and the solvent was recovered by distillation under vacuum. The results obtained are listed under Trial 1 and Trial 2 in Table 1.

TABLE 1

| Trial # | 1 | 2 | 3 | 4 |
|---|---|---|---|---|
| AR: DMAc equivalents | 2 | 2 | 2.5 | 2.5 |
| % DMF recovered | 87.2 | 90.5 | 84.8 | 88.0 |
| % DMAc present in recovered DMF | 0.33 | 0.54 | 0.00 | 0.03 |

Example 3

A 250 mL round bottom flask equipped with a stir bar was charged with 16.1 grams of Arnold's Reagent (0.126 mol). Crude DMF (100.0 grams) containing 4.4% by weight DMAc (50.4 mmol) was added at room temperature. After addition was complete, mixture was stirred for 2 hours, and the solvent was recovered by distillation under vacuum. The results obtained are listed under Trial 3 and Trial 4 in Table 1.

Examples 2 and 3 (Trials 1-4) demonstrate the effect of the amount of Arnold's Reagent relative to the amount of DMAc on the efficacy of removing DMAc as a contaminant from DMF. In Trials 1 and 2, where Arnold's Reagent was used in an equivalents ratio of 2/1 relative to DMAc, the DMAc content in the recovered DMF dropped to 0.33-0.54% by weight. However, when the ratio of Arnold's Reagent/DMAc was increased to 2.5/1, no DMAc was observed in Trial 3 while there was a trace of DMAc in the recovered DMF in Trial 4.

Example 4

A 250 mL multineck flask equipped with a stir bar, a thermometer and a 50 mL addition funnel was charged with 23.2 g of Arnold's Reagent (0.181 mols) suspended in 25 mL of DMF. The suspension was cooled to 3° C. A mixture was prepared by dissolving 20.0 g of sucrose-6-acetate (20.2% wt/wt assay) and 1.97 g of DMAc (22.6 mmols) in 15 mL of DMF (total DMAc content is 5% of DMF added by weight). This mixture was added slowly to the suspension over a period of 20 minutes. After addition was complete, the mixture was allowed to warm slowly to room temperature overnight. The reaction mixture was heated to 105° C. over a period of 1 hour then held at this temperature for an additional period of 5 hours. The reaction mixture was cooled to room temperature then quenched by dual stream quench method at pH 9.75 at 20° C. using 11% NaOH and 50 g of 1:1 DMF/water heel. The mixture was assayed for 4,1',6'-trichlorogalactosucrose (TGS6A). This procedure was performed a total of three times. The average yield of TGS6A in the three runs was 70.0%.

Example 5 (Comparative)

A 250 mL multineck flask equipped with a stir bar, a thermometer and a 50 mL addition funnel was charged with 14.2 g of Arnold's Reagent (0.111 mols) suspended in 25 mL of DMF. The suspension was cooled to 3° C. A mixture was prepared by dissolving 20.0 g of sucrose-6-acetate (20.2% wt/wt assay) in 15 mL of DMF. This mixture was added slowly to the suspension over a period of 20 minutes. After addition was complete, the mixture was allowed to warm slowly to room temperature overnight. The reaction mixture was heated to 105° C. over a period of 1 hour then held at this temperature for an additional period of 5 hours. The reaction mixture was cooled to room temperature then quenched by a dual stream quench method at pH 9.75 at 20° C. using 11% NaOH and 50 g of a 1:1 DMF/water heel. The mixture was assayed for 4,1',6'-trichlorogalactosucrose (TGS6A). This procedure was performed a total of three times. The average yield of TGS6A in the three runs was 68.6%.

Examples 4 and 5 demonstrate the advantages of carrying out the chlorination of S6A (sucrose-6-acetate) to make TGS6A (4,1',6'-trichlorogalactosucrose) in the presence of DMAc (present as a contaminant in the DMF used as solvent for the chlorination) by adjusting the amount of Arnold's Reagent used to compensate for the amount of DMAc. In Example 5, which used pure DMF as the reaction solvent (i.e., DMF uncontaminated with DMAc), the average yield of TGS6A was 68.6%. Prior studies had found that a dramatic decrease in TGS6A yield would result if this procedure were to be repeated using DMF contaminated with 5 weight % DMAc. However, Example 4 shows that if an additional amount of Arnold's Reagent is employed (to provide a DMAc/Arnold's Reagent equivalents ratio of 1/3 in addition to the normal amount of chlorinating agent used in Example 5), the chlorination reaction was found to proceed with complete yield preservation.

What is claimed:
1. A process comprising:
   a) recovering a crude recycle solvent stream comprising a tertiary formamide and a tertiary acetamide from a mixture comprising at least one substance less volatile than the tertiary formamide and the tertiary acetamide, said tertiary formamide and said tertiary acetamide;
   b) reducing the concentration of tertiary acetamide in the crude recycle solvent stream by reacting at least a portion of the tertiary acetamide with a chlorinating agent selected from the group consisting of chloroiminium species, acyl chlorides phosphorus chlorides and sulfur chlorides to provide a purified recycle solvent stream; and
   c) recycling said purified recycle solvent stream as a reaction vehicle.
2. The process of claim 1, wherein the at least one substance less volatile than the tertiary formamide and the tertiary acetamide includes at least one sucrose moiety-containing compound.
3. The process of claim 1, wherein said purified recycle solvent stream is recycled as a reaction vehicle in a sucrose-6-acylate chlorination.

4. The process of claim 1, wherein said mixture has been obtained by chlorination of a sucrose-6-acylate in a reaction vehicle comprising tertiary formamide.

5. A method comprising contacting a contaminated tertiary formamide containing a tertiary acetamide as a contaminant with a chlorinating agent selected from the group consisting of chloroiminium species, acyl chlorides, phosphorus chlorides and sulfur chlorides to react the tertiary acetamide with the chlorinating agent to form a reaction product mixture.

6. The method of claim 5 additionally comprising carrying out chlorination of a sucrose-6-acylate using said reaction product mixture as a reaction vehicle for said chlorination.

7. The method of claim 6 additionally comprising recovering said tertiary formamide by distillation following said chlorination.

8. The method of claim 6 wherein said chlorinating agent is used for said chlorination of said sucrose-6-acylate.

9. The method of claim 6 wherein said sucrose-6-acylate is sucrose-6-acetate or sucrose-6-benzoate.

10. The method of claim 5 wherein said tertiary formamide is dimethylformamide.

11. The method of claim 5 wherein said chlorinating agent is a chloroiminium species.

12. The method of claim 5 wherein said chlorinating agent is N,N-dimethylchloroformiminium chloride.

13. The method of claim 5 wherein said chlorinating agent is a chloroformiminium chloride.

14. The method of claim 11 wherein said chloroiminium species is formed in situ in said contaminated tertiary formamide by reacting said tertiary formamide with a chlorinating agent selected from the group consisting of phosgene, phosgene dimer, phosgene trimer, phosphorus pentachloride, thionyl chloride, and oxalyl chloride.

15. The method of claim 5 wherein an amount of said chlorinating agent is used so as to provide an equivalents ratio of chlorinating agent:tertiary acetamide of at least 1.5:1.

16. The method of claim 5 wherein an amount of said chlorinating agent is used so as to provide an equivalents ratio of chlorinating agent:tertiary acetamide of about 2:1 to about 3.5:1.

17. The method of claim 5 wherein said contacting is carried out within a temperature range of from about −10° C. to about 40° C.

18. The method of claim 5 wherein said tertiary acetamide is present in said contaminated tertiary formamide at a concentration of from about 0.5 to about 7 weight percent.

19. A method for producing a sucralose-6-acylate, said method comprising:
   a). forming a mixture of a sucrose-6-acylate in a reaction vehicle comprised of a tertiary formamide and a tertiary acetamide;
   b). analyzing said reaction vehicle or said mixture to determine the amount of tertiary acetamide contained therein; and
   c). contacting said mixture with a quantity of a chlorinating agent selected from the group consisting of chloroiminium species, acyl chlorides, phosphorus chlorides and sulfur chlorides to react said tertiary acetamide and said sucrose-6-acylate with said chlorinating agent, wherein said quantity of said chlorinating agent is selected in accordance with the amount of tertiary acetamide contained in said reaction vehicle or said mixture.

20. The method of claim 19, wherein said mixture is contacted with said chlorinating agent under a first set of conditions effective to react said chlorinating agent with said tertiary acetamide and then under a second set of conditions effective to chlorinate said sucrose-6-acylate.

21. The method of claim 19, wherein a molar amount of said chlorinating agent is used that is within the range:

[7·1/n·(molar amount sucrose-6-acylate)+2·1/n·(molar amount tertiary acetamide)] to

[8·1/n·(molar amount sucrose-6-acylate)+3.5·1/n·(molar amount tertiary acetamide)]

wherein n is the number of chlorine atoms per molecule of chlorinating agent that are capable of participating in a chlorination reaction with the sucrose-6-acylate and the tertiary acetamide.

22. The method of claim 19, wherein following said contacting said tertiary formamide is recovered by distillation.

23. The method of claim 19, wherein said contacting provides an initial reaction mixture which is treated with an aqueous base.

24. The method of claim 23, wherein said tertiary formamide is recovered by distillation prior to treatment of said initial reaction mixture with said aqueous base.

25. The method of claim 23, wherein said tertiary formamide is recovered after treatment of said initial reaction mixture with said aqueous base.

26. The method of claim 19 wherein said sucrose-6-acylate is sucrose-6-acetate or sucrose-6-benzoate.

27. The method of claim 19 wherein said tertiary formamide is dimethylformamide.

28. The method of claim 19 wherein said chlorinating agent is a chloroformiminium chloride.

29. The method of claim 19 wherein said chlorinating agent is N,N-dimethylchloroformiminium chloride.

30. The method of claim 19 wherein said chlorinating agent is a chloroiminium species.

31. The method of claim 30 wherein said chloroiminium species is formed in situ in said mixture by reacting said tertiary formamide with a chlorinating agent selected from the group consisting of phosgene, phosgene dimer, phosgene trimer, phosphorus pentachloride, thionyl chloride, and oxalyl chloride.

* * * * *